(12) United States Patent
McDaniels

(10) Patent No.: US 11,471,615 B2
(45) Date of Patent: Oct. 18, 2022

(54) DEVICE FOR ASSISTING SUBCUTANEOUS INJECTIONS

(71) Applicant: Christina McDaniels, San Diego, CA (US)

(72) Inventor: Christina McDaniels, San Diego, CA (US)

(*) Notice: Subject to any disclaimer, the term of this patent is extended or adjusted under 35 U.S.C. 154(b) by 283 days.

(21) Appl. No.: 16/714,024

(22) Filed: Dec. 13, 2019

(65) Prior Publication Data

US 2020/0188609 A1 Jun. 18, 2020

Related U.S. Application Data

(60) Provisional application No. 62/780,215, filed on Dec. 15, 2018.

(51) Int. Cl.
*A61M 5/32* (2006.01)
*A61M 5/42* (2006.01)

(52) U.S. Cl.
CPC .......... *A61M 5/3287* (2013.01); *A61M 5/425* (2013.01); *A61M 5/427* (2013.01)

(58) Field of Classification Search
CPC ..... A61M 5/3287; A61M 5/425; A61M 5/427
See application file for complete search history.

(56) References Cited

U.S. PATENT DOCUMENTS

| | | | |
|---|---|---|---|
| 6,902,554 B2 | 6/2005 | Huttner | |
| 2015/0157787 A1* | 6/2015 | Cully | A61M 5/46 604/6.05 |
| 2016/0022923 A1* | 1/2016 | Curtis | A61M 5/425 604/174 |
| 2016/0331910 A1* | 11/2016 | Imai | A61M 5/3293 |
| 2017/0232209 A1* | 8/2017 | Michels | A61M 5/425 604/115 |
| 2017/0273713 A1* | 9/2017 | Shah | A61M 25/0606 |

FOREIGN PATENT DOCUMENTS

DE 387465 C * 2/1932

\* cited by examiner

*Primary Examiner* — James D Ponton
(74) *Attorney, Agent, or Firm* — CP Law Group PC; Cy Bates

(57) ABSTRACT

A device for assisting a subcutaneous injection is disclosed. The device includes features which prevent an unwanted needle stick and assist the gripping of tissue for performing a safe and effective subcutaneous injection.

17 Claims, 3 Drawing Sheets

METHOD FOR ADMINISTERING A SUBCUTANEOUS INJECTION providing a device comprising: a cylindrical body having an aperture extending therethrough; a flange extending from the cylindrical body at a first side thereof, the flange and the cylindrical body forming a funnel element for guiding a syringe; and first and second skin-contacting elements extending from the cylindrical body at a second side thereof opposite the first side;

gripping tissue of a patient at an injection site associated with the subcutaneous injection using the first and second skin-contacting elements of the device;

inserting a needle-containing end of a syringe system through the funnel element toward the injection site; and

delivering the subcutaneous injection using the syringe system.

DEVICE FOR ASSISTING SUBCUTANEOUS INJECTIONS

CROSS-REFERENCE TO RELATED APPLICATIONS

This application claims benefit of priority with U.S. Provisional Ser. No. 62/780,215, filed Dec. 15, 2018; the entire contents of which are hereby incorporated by reference.

BACKGROUND

Field of the Invention

This invention relates to medical devices; and more particularly, to a hand-operated medical device for use with the administration of a subcutaneous injection, namely, to aid in the gripping of biological tissue and administering such subcutaneous injection in an effective and safe manner.

Description of the Related Art

Accidental needle sticks are common in the health care field. The Needlestick Safety Act requires employers to identify and implement safer medical devices as set forth in the Occupational Safety & Health Administration (OSHA)'s Bloodborne Pathogens Standard. Despite this legislation, the Centers for Disease Control and Prevention (CDC) estimates that 385,000 sharps-related injuries continue to occur in hospitals each year. According to the CDC's "Summary Report for Blood and Body Fluid Exposure Data Collected from Participating Healthcare Facilities" (June 1995 through December 2007), the majority of percutaneous injuries involving hollow-bore needles occurred during use of the device, one-third of all percutaneous injuries involved a hypodermic needle attached to a syringe, and over one-fourth of injuries involving hollow-bore needles happened as the needle was introduced, adjusted, or taken out of the patient. While many needleless devices are available, some items in a hospital setting cannot be changed to needleless devices. For example, subcutaneous injections of insulin require a needle for administration.

There is a need for solutions that address these and other problems, for example, preventing a needle stick or aiding in the gripping of tissue required for making a subcutaneous injection.

SUMMARY

A device for assisting a subcutaneous injection is disclosed.

The device includes features configured to prevent an unwanted needle stick and assist the gripping of tissue for performing a safe and effective subcutaneous injection.

While a preferred embodiment is illustrated and described herein, other similar embodiments will become apparent to one having skill in the art, including those described in U.S. Provisional Ser. No. 62/780,215, which is incorporated herein by reference.

In the preferred embodiment, the proposed device comprises the following features:

a cylindrical body having an aperture extending therethrough;

a flange extending from the cylindrical body at a first side thereof, the flange and the cylindrical body forming a funnel element for guiding a syringe or portion thereof; and first and second skin-contacting elements extending from the cylindrical body at a second side thereof opposite the first side.

In varying embodiments, each of the first and second skin-contacting elements may further comprise, in any combination, one or more of:

a spring element disposed at a proximal end and configured to couple with the cylindrical body;

a gripping element disposed at a distal end; and an elongated element disposed between the spring element and the gripping element.

In some embodiments, the device may further comprise:

one or more texture elements disposed on one or more surfaces of the elongated element, the gripping element, or a combination thereof.

BRIEF DESCRIPTION OF THE DRAWINGS

These, and other features and embodiments, will be further appreciated in the appended detailed descriptions, in particular, when reviewed in conjunction with the drawings, wherein:

FIG. 3 shows a method for administering a subcutaneous injection using the device of FIGS. 1-2.

DETAILED DESCRIPTION OF EMBODIMENTS

In the following description, for purposes of explanation and not limitation, details and descriptions are set forth in order to provide a thorough understanding of the embodiments of the invention. However, it will be apparent to those skilled in the art that the present invention may be practiced in other embodiments, including certain variations or alternative combinations that depart from these details and descriptions. The illustrated examples are intended to enable those with skill in the art to practice the invention, but such examples shall not reasonably be construed as limiting the spirit and scope of the invention as-claimed.

Illustrated Embodiment

Figure 1:
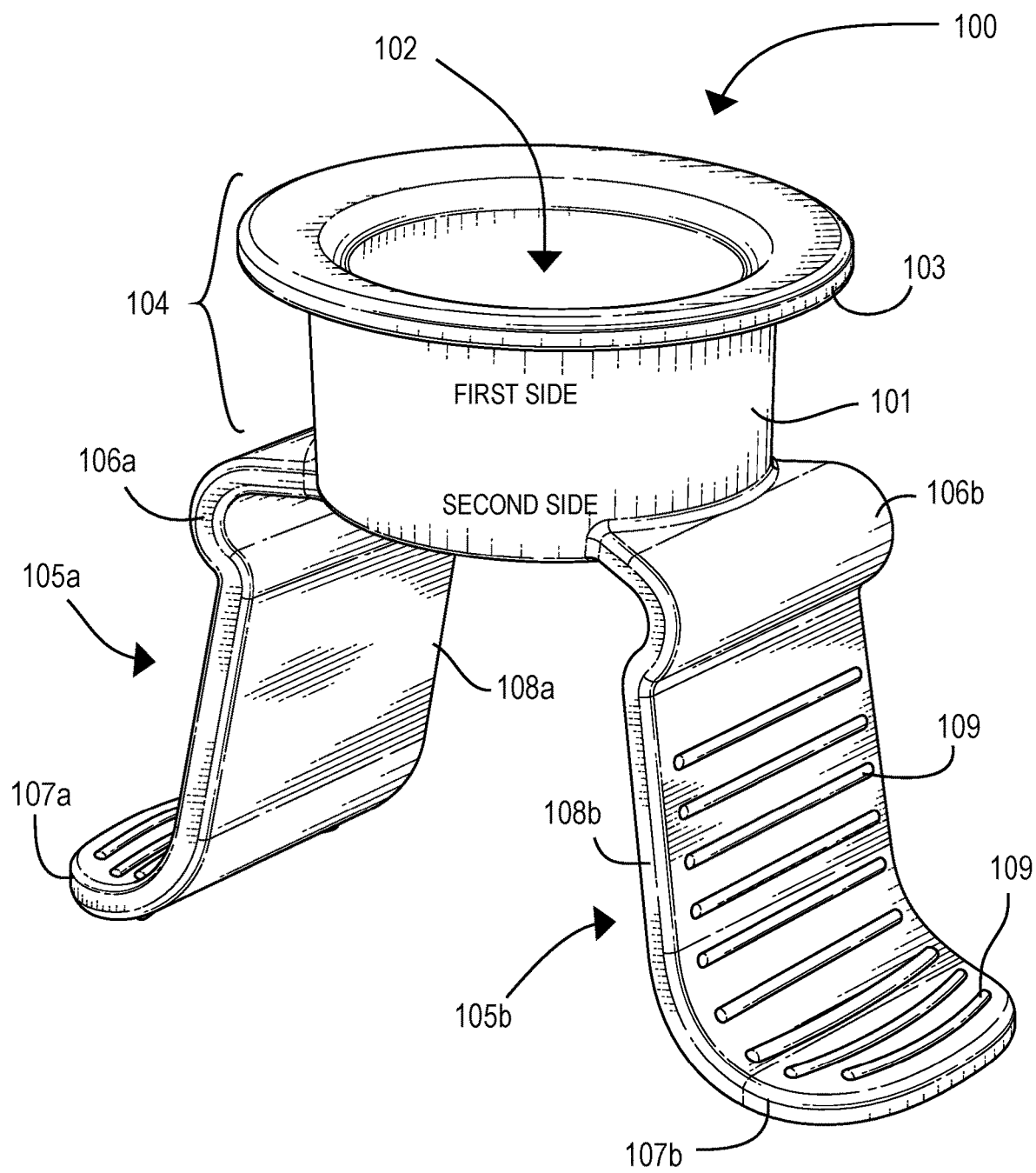
FIG. 1 shows a perspective view illustrating a top, front- and right-side of a device for assisting a subcutaneous injection in accordance with the illustrated embodiment.

Now turning to the drawings, FIG. 1 shows a perspective view illustrating a top, front- and right-side of a device 100 for assisting a subcutaneous injection in accordance with the illustrated embodiment. The device 100 includes: a cylindrical body 101 having an aperture 102 extending therethrough; a flange 103 extending from the cylindrical body at a first side thereof, the flange and the cylindrical body forming a funnel element 104 for assisting a subcutaneous injection; and first and second skin-contacting elements 105a; 105b, respectively, extending from the cylindrical body at a second side thereof opposite the first side.

In varying embodiments, including the illustrated embodiment as-shown, each of the first and second skin-contacting elements 105a; 105b, respectively, may further comprise, in any combination, one or more of: a spring element 106a; 106b, respectively, disposed at a proximal end of the respective skin-contacting element and configured to couple with the cylindrical body; a gripping element 107a; 107b disposed at a distal end of the respective skin-contacting element; and an elongated element 108a; 108b disposed between the spring element and the gripping element.

Here, the first skin-contacting element 105a comprises: a first spring element 106a disposed at a proximal end thereof, a first gripping element 107a disposed at a distal end thereof, and a first elongated element 108a disposed between the first spring element and the first gripping element. Moreover, the second skin-contacting element 105b comprises: a second spring element 106b disposed at a proximal end thereof, a second gripping element 107b disposed at a distal end thereof, and a second elongated element 108b disposed between the second spring element and the second gripping element.

In some embodiments, including the illustrated embodiment, each skin-contacting element of the device may further comprise: one or more texture elements 109 disposed on one or more surfaces of the elongated element, the gripping element, or a combination thereof.

Figure 2:
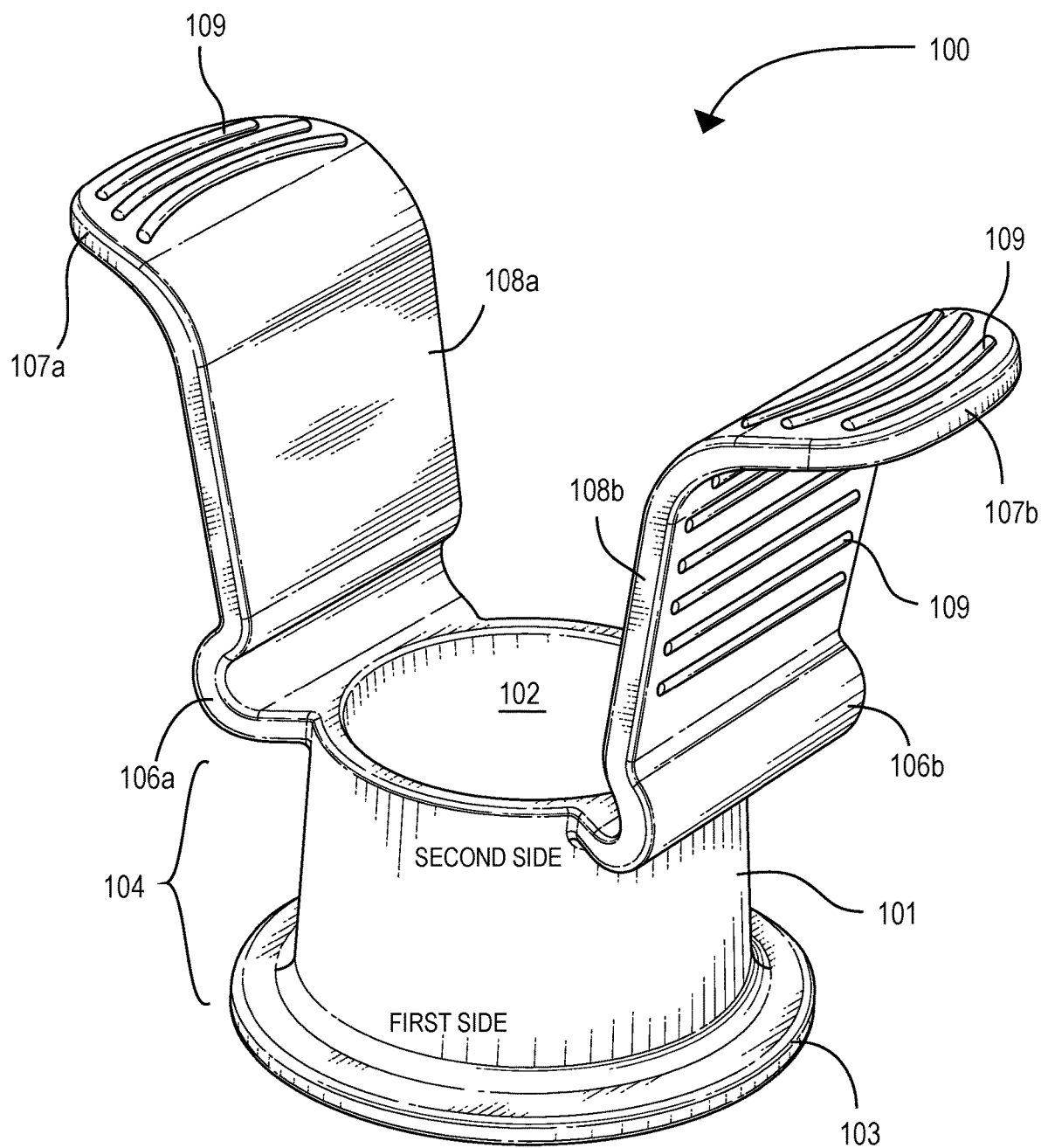
FIG. 2 shows a perspective view illustrating a bottom, rear- and left-side of the device for assisting a subcutaneous injection in accordance with the illustrated embodiment.

FIG. 2 shows a perspective view illustrating a bottom, rear- and left-side of the device 100 for assisting a subcutaneous injection in accordance with the illustrated embodiment. Here, the features as previously described are viewed from an alternative perspective.

The device is preferably manufactured using a conventional injection molding technique and therefore can comprise a thermoplastic material, such as acrylonitrile butadiene styrene (ABS), polycarbonate, or other thermoplastic material. Other manufacturing techniques and material compositions will be apparent to one having skill in the art and may be alternatively practiced.

In accordance with a related aspect of the invention, a method for using the above-described device is disclosed, such use including administering a subcutaneous injection. The method comprises, in order: (i) providing a device comprising: a cylindrical body having an aperture extending therethrough; a flange extending from the cylindrical body at a first side thereof, the flange and the cylindrical body forming a funnel element for guiding a syringe; and first and second skin-contacting elements extending from the cylindrical body at a second side thereof opposite the first side; (ii) gripping tissue of a patient at an injection site associated with the subcutaneous injection using the first and second skin-contacting elements of the device; (iii) inserting a needle-containing end of a syringe system through the funnel element toward the injection site; and (iv) delivering the subcutaneous injection using the syringe system.

While various details, features, and combinations are described in the instant disclosure, one having skill in the art will appreciate a myriad of possible alternative combinations and arrangements of the features disclosed herein. As such, the descriptions are intended to be enabling only, and non-limiting. Instead, the spirit and scope of the invention is set forth in the appended claims.

FEATURE LIST device 100
cylindrical body 101
aperture 102
flange 103
funnel element 104
first skin-contacting element 105a
second skin-contacting element 105b
first spring element 106a
second spring element 106b
first gripping element 107a
second gripping element 107b
first elongated element 108a
second elongated element 108b
texture element 109

What is claimed is:

1. A device for assisting a subcutaneous injection, the device comprising:
  a cylindrical body having an aperture extending therethrough;
  a flange extending from a first side of the cylindrical body, the flange and the cylindrical body forming a funnel element for guiding a syringe; and
  first and second skin-contacting elements extending from a second side of the cylindrical body opposite the first side;
  each of the first and second skin-contacting elements further comprising:
    a proximal end and a distal end opposite the proximal end, wherein the proximal end is coupled to the cylindrical body,
    a spring element disposed at the proximal end,
    a gripping element disposed at the distal end,
    an elongated element disposed between the spring element and the gripping element, the elongated element comprising a proximal elongated end and a distal elongated end opposite the proximal elongated end, wherein the proximal elongated end is coupled to the spring element and the distal elongated end is coupled to the gripping element, and
    one or more texture elements disposed on one or more surfaces of the elongated element, the gripping element, or a combination thereof.

2. The device of claim 1, wherein the first skin-contacting element is coupled to a portion of the cylindrical body opposite the second skin-contacting element.

3. The device of claim 1, wherein the spring element of the first skin-contacting element is separate and distinct from the spring element of the second skin-contacting element.

4. The device of claim 1, wherein the spring element of the first skin-contacting element is integrated with the proximal end of the first skin-contacting element.

5. The device of claim 1, wherein the spring element of the second skin-contacting element is integrated with the proximal end of the second skin-contacting element.

6. The device of claim 1, wherein the first skin-contacting element and the second skin-contacting element are each non-removably coupled to the cylindrical body.

7. The device of claim 1, wherein the first skin-contacting element and the second skin-contacting element are each coupled at a bottom surface of the cylindrical body.

8. The device of claim 1, wherein each distal end of the first and second skin-contacting elements comprises a curved portion.

9. A device for assisting a subcutaneous injection, the device comprising:
  a cylindrical body having an aperture extending therethrough;
  a flange extending from a first side of the cylindrical body, the flange and the cylindrical body forming a funnel element for guiding a syringe; and
  first and second skin-contacting elements coupled to the cylindrical body;
  each of the first and second skin-contacting elements further comprising:
    a proximal end and a distal end opposite the proximal end, wherein the proximal end is coupled to the cylindrical body, one or more texture elements disposed on one or more surfaces of each of the first and second skin-contacting elements,
a spring element disposed at the proximal end configured to couple with the cylindrical body, and
a gripping element disposed at the distal end.

10. The device of claim 9, each of the first and second skin-contacting elements further comprising:
an elongated element disposed between the spring element and the gripping element.

11. The device of claim 9, wherein the first skin-contacting element is coupled to a portion of the cylindrical body opposite the second skin-contacting element.

12. The device of claim 9, wherein the spring element of the first skin-contacting element is separate and distinct from the spring element of the second skin-contacting element.

13. The device of claim 9, wherein the spring element of the first skin-contacting element is integrated with the proximal end of the first skin-contacting element.

14. The device of claim 9, wherein the spring element of the second skin-contacting element is integrated with the proximal end of the second skin-contacting element.

15. The device of claim 9, wherein the first skin-contacting element and the second skin-contacting element are each non-removably coupled to the cylindrical body.

16. The device of claim 9, wherein the first skin-contacting element and the second skin-contacting element are each coupled at a bottom surface of the cylindrical body.

17. The device of claim 9, wherein each distal end of the first and second skin-contacting elements comprises a curved portion.

* * * * *